US005792935A

United States Patent [19]
Arntzen et al.

[11] Patent Number: 5,792,935
[45] Date of Patent: Aug. 11, 1998

[54] AGROBACTERIUM TUMEFACIENS TRANSFORMATION OF MUSA SPECIES

[75] Inventors: Charles J. Arntzen; Gregory D. May, both of Tompkins. N.Y.

[73] Assignee: Texas A&M University, College Station, Tex.

[21] Appl. No.: 652,521

[22] PCT Filed: Dec. 9, 1994

[86] PCT No.: PCT/US94/14210

§ 371 Date: Jun. 5, 1996

§ 102(e) Date: Jun. 5, 1996

[87] PCT Pub. No.: WO95/15678

PCT Pub. Date: Jun. 15, 1995

Related U.S. Application Data

[63] Continuation of Ser. No. 341,461, Nov. 17, 1994, abandoned, which is a continuation of Ser. No. 164,296, Dec. 9, 1993, abandoned.

[51] Int. Cl.$^6$ .............. A01H 5/00; C12N 15/18; C12N 15/24; C12N 15/82
[52] U.S. Cl. .............. 800/205; 800/DIG. 52; 800/DIG. 65; 435/69.1; 435/69.3; 435/69.4; 435/69.51; 435/69.52; 435/69.6; 435/69.7; 435/172.3; 435/252.2; 435/418
[58] Field of Search .............. 435/69.1, 69.3, 435/69.4, 69.51, 69.52, 69.6, 69.7, 172.3, 252.2, 418; 800/205, DIG. 52, DIG. 65

[56] References Cited

U.S. PATENT DOCUMENTS

| | | | |
|---|---|---|---|
| 4,769,061 | 9/1988 | Comai | 71/86 |
| 4,801,540 | 1/1989 | Hiatt et al. | 435/172.3 |
| 4,956,282 | 9/1990 | Goodman et al. | 435/172.3 |
| 5,004,863 | 4/1991 | Umbeck | 800/205 |
| 5,015,580 | 5/1991 | Christou et al. | 435/172.3 |
| 5,049,500 | 9/1991 | Arnizen et al. | 435/172.3 |
| 5,102,796 | 4/1992 | Hall et al. | 435/172.3 |
| 5,107,065 | 4/1992 | Shewmaker et al. | 800/205 |
| 5,164,310 | 11/1992 | Smith et al. | 435/172.3 |
| 5,177,010 | 1/1993 | Goldman et al. | 435/172.3 |
| 5,187,073 | 2/1993 | Goldman et al. | 435/172.3 |
| 5,231,020 | 7/1993 | Jorgensen et al. | 435/172.3 |

FOREIGN PATENT DOCUMENTS

| | | | |
|---|---|---|---|
| 267159A2 | 5/1988 | European Pat. Off. . | |
| 486233A2 | 5/1992 | European Pat. Off. . | |
| 9004462 | 2/1991 | WIPO . | |
| WO9102071 | 2/1991 | WIPO | C12N 15/82 |
| 9100183 | 7/1991 | WIPO . | |
| WO9110725 | 7/1991 | WIPO | C12N 5/00 |
| WO9420135 | 9/1994 | WIPO . | |

OTHER PUBLICATIONS

M. De Cleene. *The Susceptibility of Monocotyledons to Agrobacterium tumefaciens*, Phytopathologische Zeitschrift Journal of Phytopathology, vol. 113(1). pp. 1–9 (1985).

Frontiers of Infectious Diseases. New Strategies in Parasitology. Proceedings of an International Symposium Sponsored by Glaxo Research. Brocket Hall. Hertfordshire. Apr. 22–25, 1989.

*Plant Physiology*, vol. 95, issued 1991. J. Gould, et al., "Transformation of *Zea mays* L. Using *Agrobacterium tumefaciens* and the Shoot Apex". pp. 426–434.

*The Plant Cell*, vol. 2, issued Jul. 1990. W.J. Gordon-Kamm, et al.. "Transformation of Maize Cells and Regeneration of the Fertile Transgenic Plants", pp. 603–618.

*Bio/Technology*, vol. 7, No. 2, issued Feb. 1989. F. J. Novak, et al., "Somatic Embryogenesis and Plant Regeneration in Suspension Cultures of Dessert (AA and AAA) and Cooking (ABB) Bananas (Musa spp.)". pp. 154–159.

W. R. Sharp, et al., "Handbook of Plant Cell Culture. vol. 2", published 1984 by Macmillan Publishing Company (N.Y.), pp. 327–348.

Arntzen, C.J. et al. "Production of Candidate Oral Vaccines in Edible Tissues of Transgenic Plants." *Vaccines* 339–344 (1994).

Bouhida, Mohammed et al. "An analysis of the complete sequence of a sugarcane bacilliform virus genome infectious to banana and rice." *Journal of General Virology* 74:15–22 (1993).

Sagi, Laszlo et al. "Transient gene expression in electroporated banana (Musa ssp., cv. 'Bluggoe', ABB group) protoplasts isolated from regenerable embryogenetic cell suspensions." *Plant Cell Reports* 13:262–266 (1994).

Swennen, R.L. "De veredeling van de banaan voor resistentie tegen de bladschimmel *Mycosphaerella fijiensis*." *Bull. Séanc. Acad. r. Sci. Outre–Mer Meded. Zitt. K. Acad. overzeese Wet.* 39(1993–4):567–576 (1994).

Commonwealth Agricultural Bureau Database. DN 881669567. XP002025264. Oct. 13–17, 1986.

Databse WPI. Section. Ch. Week 9503. XP002025266. Oct. 24, 1994.

R.D. Huggan "Are Bananas and Plantains Catching Up" *Biotechnology and Development Monitor* 14:14–16 (1993).

R. Haicour et al. "Further Information on Protoplast Regeneration and Transformation in Musa " Proceedings of the Workshop on Biotechnology Applications for Banana and Plantain Improvement San Jose, Costa Rica (Jan. 27–31, 1992).

(List continued on next page.)

*Primary Examiner*—David T. Fox
*Attorney, Agent, or Firm*—James Remenick; Baker & Botts, L.L.P.

[57] ABSTRACT

Methods are provided for transforming Musa plants. In particular, methods for wounding meristematic Musa plant tissue to facilitate access of *Agrobacterium tumefaciens* comprising genetically-engineered T-DNA is provided. The methods may be used to transform the plant to produce pharmaceutical products or to alter the phenotypic trait of the fruit of the plant.

30 Claims, 2 Drawing Sheets

OTHER PUBLICATIONS

W.H. Shen et al. "T–DNA Transfer to Maize Cells: Histochemical Investigation of β–Glucuronidase Activity in Maize Tissues" *Proc. Natl. Acad. Sci. USA* 90:1488–1492 (1993).

I. Potrykus "Gene Transfer to Cereals: An Assessment" *Bio/Technology* Jun.:535–542 (1990).

A. Wilmink et al. "Selective Agents and Marker Genes for Use in Transformation of Monocotyledonous Plants" *Plant Molec. Biol. Rep.* 11:165–185, No. 2 (1993).

V. Vasil et al. "Herbicide Restistance Fertile Transgenic Wheat Plants Obtained by Microprojectile Bombardment of Regenerable Embryogenic Callus" *Bio/Technology* 10:667–674 (1992).

N.H. Grimsley et al. "Meristematic Tissues of Maize Plants are Most Susceptible to Agroinfection with Maize Streak Virus" *Bio/Technology* 6:185–189 (1988).

W. Schafer et al. "T–DNA Integration and Expression in a Monocot Crop Plant After Induction of Agrobacterium" *Nature* 327:529–532 (1987).

F.J. Novak et al. "Somatic Embryogenesis and Plant Regeneration in Suspension Cultures of Dessert (AA AND AAA) and Cooking (ABB) Bananas (Musa SPP.)."*Bio/Technology* 7:154–159 (1989).

S.D. Kung et al. (Eds.) in *Plant Biotechnology* chps. 1–6,18 (Butterworths)(1989).

Recomendations from the INIBAP Workshop on "Biotechnology for Banana and Plantain" San Jose, Costa Rica (Jan. 27–31, 1992).

M.D. Chilton "Agrobacterium Gene Transfer: Progress on a 'Poor Man's Vector' for Maize" *Proc. Natl. Acad. Sci. USA* 90:3119–3120 (1993).

W. Zhang et al. "Efficient Regeneration of Transgenic Plants from Rice Protoplasts and Correctly Regulated Expression of the Foreign Gene in the Plants" *Theor. Appl. Genet.* 76:835–840 (1988).

K. Toriyama et al. "Transgenic Rice Plants After Direct Gene Transfer into Protoplasts" *Bio/Technology* 6:1072–1074 (1988).

C.A. Rhodes et al. "Genetically Transformed Maize Plants from Protoplasts" *Sci.* 240:204–207 (1988).

D.E. McCabe et al. "Stable Transformation of Soybean (*Glycine max*) by Particle Acceleration" *Bio/Technology* 6:923–926 (1988).

G. An "Binary Ti Vectors for Plant Transformation and Promoter Analysis" *Meth. Enz.* 153:292–305 (1987).

P. Umbeck et al. "Genetically Transformed Cotton (*Gossypium hirsutum* l. ) Plants" *Bio/Technology* 5:263–266 (1987).

E.A. Shahin et al. "Gene Transfer System for Potato" *Hort. Sci.* 21:1199–1201, No. 5 (1986).

S.K. Datta et al. "Genetically Engineered Fertile India-Rice Recovered from Protoplasts" *Bio/Technology* 8:736–740 (1990).

J.D. Watson et al. "Genetic Engineering of Plants by Using Crown Gall Plasmids" in *Recombinant DNA A Short Course* Scientific American Books (1983).

T.M. Klein et al. "Applications of the Particle Gun in Plant Biology" in *Progress in Plant Cellular and Molecular Biology*, 56–66, H.J.J. Nijkamp et al. (Eds.), Kluwer Academic Pub. (1990).

H.J. Klee et al. "Transformation of Plants by *Agrobacterium tumefaciens*" in *Cell Culture and Somatic Cell Genetics of Plants*, 6:2–23, J. Schell et al. (Eds.), Academic Press.

M.A.W. Hinchee et al. "Production of Transgenic Soybean Plants Using Agrobacterium–Medicated DNA Transfer" *Bio/Technology* 6:915–922 (1988).

D.M. Raineri et al. "Agrobacterium–Medicated Transformation of Rice (*Oryza sativa* l.)" *Bio/Technology* 8:33–38 (1990).

W.J. Gordon–Kamm et al. "Transformation of Maize Cells and Regeneration of Fertile Transgenic Plants" *The Plant Cell* 2:603–618 (1990).

I. Potrykus "Gene Transfer to Plants: Assessment of Published Approaches and Results" *Annu. Rev. Plant Physiol. Plant Mol. Biol.* 42:205–225 (1991).

K. Shimamoto et al. "Fertile Transgenic Rice Plants Regenerated from Transformed Protoplasts" *Nature* 338:274–276 (1989).

H. Klee et al. "Agrobacterium–Mediated Plant Transformation and its Further Applications to Plant Biology" *Ann. Rev. Plant Physiol.* 38:467–486 (1987).

J. Paszkowski et al. "General Introduction" in *Cell Culture and Somatic Cell Genetics of Plants*, 6:52–68, J. Schell et al. (Eds.), Academic Press.

J.M.J. De Wet et al. "Exogenous Gene Transfer in Maize (*Zea mays*) Using DNA Treated Pollen" in *The Experimental Manipulation of Ovule Tissues*, G.P. Chapman et al (Eds.), Longman.

G. Neuhaus et al. "Plant Transformation by Microinjection Techniques" *Physiol. Plant.* 79:213–217 (1990).

Y. Ohta "High–Efficiency Genetic Transformation of Maize by a Mixture of Pollen and Exogenous DNA" *Proc. Natl. Acad. Sci. USA* 83:715–719 (1986).

J. Futterer et al. "Cauliflower Mosiac Virus as a Gene Expression Vector for Plants" *Physiol. Plant.* 79:154–157 (1990).

D. Hess "Pollen–Based Techniques in Genetic Manipulation" *Intl. Rev. Cytol.* 107:367–395 (1987).

T.M. Klein et al. "Factors Influencing Gene Delivery into *Zea mays* Cells by High–Velocity Microprojectiles" *Bio/Technology* 6:559–563 (1988).

M.E. Fromm et al. "Stable Transformation of Maize After Gene Transfer by Electroporation" *Nature* 319:791–793 (1986).

H.M. Zhang et al. "Transgenic Rice Plants Produced by Electroporation–Mediated Plasmid Uptake into Protoplasts" *Plant Cell Rep.* 7:379–384 (1988).

G. Neuhaus et al. "Transgenic Rapeseed Plants Obtained by the Microinjection of DNA into Microspore–Derived Embryoids" *Theor. Appl. Genet.* 75:30–36 (1987).

AGROBACTERIUM TUMEFACIENS TRANSFORMATION OF MUSA SPECIES

REFERENCE TO RELATED APPLICATIONS

This patent application is a continuation of abandoned U.S. patent application Ser. No. 08/341,461, filed Nov. 17, 1994, which is a continuation of abandoned U.S. patent application Ser. No. 08/164,296, filed Dec. 9, 1993.

BACKGROUND OF THE INVENTION

1. Field of the Invention

This invention relates to methods for transforming Musa species such as bananas or plantains using *Agrobacterium tumefaciens*.

2. Description of the Prior Art

Bananas and plantains are perennial giant herbs belonging to the Genus Musa; their fruits are the fourth most important food in the developing world. Approximately 10% of the world's production of bananas (over 9 million tons in 1990, at a value of over U.S. $4 billion) enters the export market to generate an important source of income for tropical and subtropical regions. In light of the fact that Musa spp. make such an enormous contribution to food security and also provide export revenue in developing countries, it is a remarkable paradox that these crops have never benefited from traditional crop breeding. Production around the world is entirely dependent on unimproved clones that were often collected from nature, domesticated and maintained by clonal propagation. In terms of important crops for which biotechnology offers the possibility for dramatic genetic improvement, there are few opportunities as open for novel approaches as Musa spp.

There is general agreement that edible bananas originated from the two species, *M. accuminata* and *M. balbisiana*. Edible bananas have three different ploidy levels: 2N=22, 3N=33 and 4N=44. They have been propagated vegetatively for hundreds of years, with somatic mutations providing variability. Triploids are the most numerous and widely utilized cultivars (including dessert bananas used in world export trade). Efforts to breed Musa using conventional methods are fraught with obstacles, including low fertility, levels of ploidy, and lack of genetic variability. Since almost all accepted cultivars are seedless, sterile, clonally-propagated plants, conventional breeding efforts must begin with unimproved material that has been poorly characterized for genetic traits. It would be a major advantage if it were to be possible to make genetic improvements in the currently accepted seedless cultivars that are in production as food crops; this manuscript describes a system for reproducible and rapid genetic transformation of Musa that will make this possible.

Although traditional breeding has been slow for Musa spp., application of the tools of plant tissue culture have been of significant value to crop improvement. Embryo rescue, cell suspension cultures, and related cell culture techniques have been used in research activities to overcome limitations in crop breeding, with resultant selection of genetic variants with new phenotypes. Plant cells grown in unorganized (callus, cells and protoplasts) cultures undergo ubiquitous genetic change or somaclonal variation. While this genetic variability is useful in creating new germplasm, it is a distinct negative feature in the clonal propagation of desired cultivars for which genetic uniformity is necessary. This has led to development of shoot-tip culture protocols which are now widely in use in developed and developing countries for Musa multiplication. Characteristically, these micropropagation procedures require only short periods of exposure of the plant tissues to growth in an undifferentiated state, and have a very low level of somaclonal variation among progeny.

In the development of the transformation system described below, we have attempted to devise a system that would mimic the widely used shoot micropropagation procedures now in use commercially. Our goal was to make available a system that would be useful for targeted genetic modification of existing, valuable cultivars with the least possible probability of introducing unanticipated somaclonal variability.

Virulent strains of the gram negative soil bacterium *Agrobacterium tumefaciens* are known to infect dicotyledonous plants and certain monocotyledonous plants. The tumor-inducing agent in the *A. tumefaciens* is a plasmid that functions by transferring some of its DNA into its host plan's cells. This plasmid (the Ti plasmid), and the virulence of the various strains of *A. tumefaciens* is determined in part by the vir region of the Ti plasmid, which is responsible for mobilization and transfer of T-DNA. Foreign genes may be mobilized and delivered to a susceptible host via the Ti plasmid.

The Ti plasmid can be used as a vector for the genetic engineering of host plants. In most cases the native *A. tumefaciens* Ti plasmid is modified to create a disarmed plasmid, that is, one that does not cause tumor formation or disease.

It has generally been assumed that the host range of *A. tumefaciens* was limited to dicotyledous species. There has been limited success in transformation of some monocotyledous plants such as Gramineae (see U.S. Pat. Nos. 5,187, 073 and 5,177,010). Hooykaas-Van Slogteren et al., *Nature*, 311,763 (1984), reported the production of small swellings at wound sites infected with *A. tumefaciens* in monocotyledous species of the Liliaceae and Amaryllidaceae families. Hernalsteens, et al. reported [EMBO Journal, 3, 3039 (1984)] that cultured stem fragments of the monocotyledon *Asparagus officinalis*, a member of the family Liliaceae, infected with *A. tumefaciens* strain C58 developed tumorous proliferations. DeCleene and DeLey in *The Botanical Review*, 42,389 (1976) teach that monocots of the orders Liliales and Arales are susceptible to infection with *A. tumefaciens*, but that monocotyledons in general are unsusceptible to *A. tumefaciens* infection. It has been noted [Potryklus, Bio/Technology 8:515 (1990)] that monocot transformation is difficult with Agrobacterium because these species do not show the wound response characteristic of dicots (which are competent for activating vir gene expression in the bacterium, transformation, and regeneration of tissues in which the introduced genes are integrated into the plant cell chromosome). There is insufficient data available to predict the extent to which other monocots can be made susceptible to Agrobacterium. Chilton [*Proc. Natl. Acad. Sci.* 90:3119 (1993)] noted that host plant chemistry is important for the delicate chemical signaling between bacteria and plant cells. This situation has further complexity because of differences in agroinfection efficiency between different Ti plasmid vectors. Chilton teaches that there is a great deal of uncertainty in the transformation of monocots which makes it impossible to predict in advance that Musa can be transformed. Because of this uncertainty, it cannot be predicted in advance if the bacterial gene transfer will occur in other untested monocots, such as Musa.

No one has reported the transformation of any member of the monocotyledonous Musa family (such as bananas and plantains) by infection with *A. tumefaciens*. It has heretofore been generally thought that Musa species are not susceptible to transformation by *A. tumefaciens*. In fact, the prior art teaches that *A. tumefaciens* cannot be used to transform Musa. [*Biotech. and Devel. Monitr.*, 14:14–16 (1993)].

There is a need to develop a method for effecting genetic transformation of Musa. The ability to insert foreign genes into these popular tropical plants would be of great importance since it would allow attempts to create disease and pest resistance and altered fruit phenotypes via genetic engineering.

These and other advantages of the present invention will become apparent from the following detailed description.

SUMMARY OF THE INVENTION

It is an object of the present invention to provide methods for transforming Musa plants. It is also an additional object of the present invention to provide transformed Musa plants.

Accordingly, the present invention provides a method for transforming a Musa plant, said method comprising: wounding meristematic tissue from a Musa plant to generate a wounded Musa plant tissue and to facilitate access of *Agrobacterium tumefaciens* to Musa plant cells competent for transformation and regeneration; and applying to said wounded Musa plant tissue at least one transformation competent *Agrobacterium tumefaciens* to transform said Musa plant, wherein said at least one transformation competent *Agrobacterium tumefaciens* harbors at least one Ti plasmid, wherein said at least one Ti plasmid comprises at least one genetically engineered T-DNA to effect transformation of said Musa plant.

The present invention also provides a method for transforming Musa plants wherein the at least one genetically engineered T-DNA further comprises at least one second gene selected from the group consisting of genes which code for selection agent resistance, genes which code for at least one screenable marker, and combinations thereof.

The present invention also provides a method for transforming Musa plants, wherein the at least one genetically engineered T-DNA further comprises at least one gene which codes for selection agent resistance, and wherein the method further comprises regenerating the transformed Musa plant tissue in the presence of at least one selection agent responsive to the at least one gene which codes for selection agent resistance so as to select for resistant tissue transformed with the at least one genetically engineered T-DNA.

The present invention also provides a Musa plant (and progeny thereof) which includes cells which comprise in its genome at least one gene selected from the group consisting of at least one gene which codes for at least one polypeptide non-native to the Musa plant, at least one gene which codes for at least one polypeptide native to the Musa plant, at least one gene which codes for altered gene expression of at least one native Musa gene, and combinations thereof.

Also provided is a method for transforming Musa plants with at least one pharmaceutical selected from the group consisting of hepatitis B surface antigen, Norwalk virus capsid protein, insulin, interleukins, growth hormone, erythropoietin, G-CSF, GM-CSF, hPG-CSF, M-CSF, Factor VIII, Factor IX, tPA, insulin, and combinations thereof. Also provided are plants transformed with at least one pharmaceutical.

Also provided is a method for transforming Musa plants with at least one gene that changes the phenotypic trait of the fruit of the plant. Also provided are transformed plants that have fruit having an altered phenotypic trait.

Also provided is a method for transforming Musa plants so as to confer herbicide and/or disease resistance to the plants.

Also provided is a method for transforming a Musa plant wherein the transformed Musa plant is grown for a sufficient time to identify the presence of chimeric features, producing nonchimeric tissue by dividing the transformed Musa plant into segments which have at least one meristem which can regenerate into an intact plant and which have cells that are uniformly transformed to produce nonchimeric tissue, and growing the nonchimeric tissue into a nonchimeric plant.

These and other objects and advantages are described in the following Detailed Description.

DETAILED DESCRIPTION OF THE INVENTION

Figure 1:
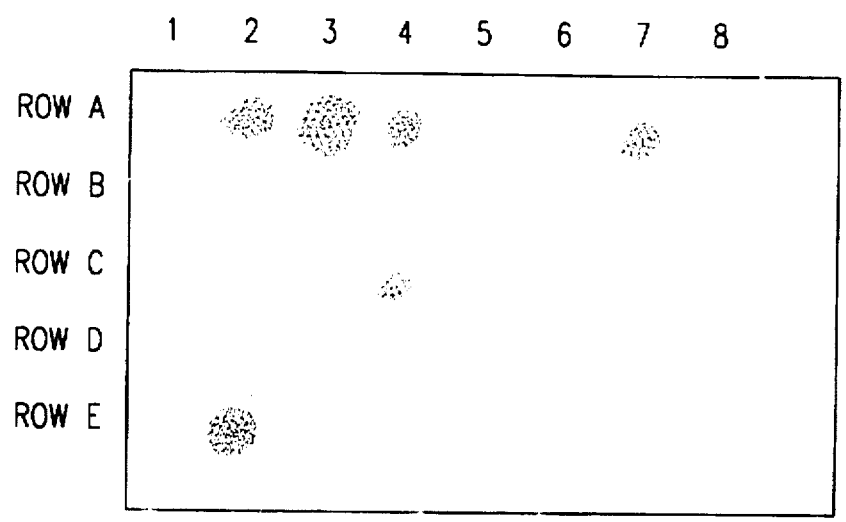
FIG. 1 depicts NFT-II dot-blot assays of individual regenerant plants following Agrobacterium-mediated genetic transformation. Each well (spot) contains an extract of leaf tissue from an individual plant. Rows A, B, and C all contain extracts from putative banana transformants recovered after selection on 100 mg/l kanamycin sulfate. Row D contains extracts from non-transformed control banana plants. Samples E-1 and E-2 are non-transformed and transformed tobacco plants, shown for comparison. Variability in intensity of the reaction among different putative regenerants is attributed to the random chromosomal insertion of the T-DNA into the banana chromosomes, with concomitant variability in levels of NPT-II expression.

The method of the present invention is for the generation of stable, transformed Musa species. The term Musa includes bananas and plantains. Suitable Musa tissues for transformation include meristematic tissue such as, but not limited to, apical meristem, adventitious meristem, and corm tissues of growing banana or plantain shoot cultures. Suitable tissue must also be capable of regeneration into at least one intact plant. Lateral or axial meristematic tissue may also be suitable.

The method involves wounding meristematic tissue (to facilitate infection by Agrobacterium tumefaciens) by techniques such as, but not limited to, dissection (e.g., longitudinal bisection), cutting, puncturing, and/or micro-particle bombardment. Wounding may be enhanced in effectiveness by micro-particle bombardment of dissected tissue. Micro-particle bombardment may be conducted by any technique known to those skilled in the art. Such techniques include, but are not limited to, tungsten or gold micro-particle bombardment. It is anticipated that wounding not only provides exposed tissue which is competent for transformation by Agrobacterium tumefaciens, but also stimulates the production of compounds which induce the virulence of the bacterium.

After wounding, meristematic tissues may be incubated for a suitable incubation time period such as about one to about eight, preferably about two to about six and most preferably about four days at a suitable incubation temperature and suitable illumination regime. Suitable incubation temperatures are about 25° C. to about 29° C., preferably about 26° C. to about 28° C., and most preferably at about 27° C. Suitable illumination regimes are about 14 hours to about 18 hours, and preferably about 15 hours to about 17 hours, and most preferably about 16 hours. In an alternative embodiment the wounded tissue is subjected to A. tumefaciens treatment without incubation beforehand.

The method involves applying to the wounded tissue at least one transformation competent A. tumefaciens to transform the plant. The selection of the appropriate A. tumefaciens strain can be made by those having skill in the art. An appropriate strain is one which can effectively deliver the gene of interest. Suitable A. tumefaciens strains include, but are not limited to, strain LBA4404, C58, and A281, harboring a plasmid which causes gene expression in Musa. The A. tumefaciens comprises at least one Ti plasmid comprising at least one genetically engineered T-DNA. A. tumefaciens may be applied by any technique known to those skilled in the art, such as, but not limited, manual application by fingertip, swabbing, injection and/or by co-cultivation.

Application of A. tumefaciens will be for a suitable time period. A suitable incubation time is about 15 to about 60 minutes, preferably about 20 to about 45 minutes, and most preferably about 30 minutes. The genetically engineered T-DNA may carry one or more genes to transform the plant. These may be, for example, at least one first gene which codes for at least one protein non-native to the Musa plant, at least one protein native to the Musa plant, at least one gene which alters gene expression in the Musa plant, and combinations thereof. The genetically engineered T-DNA may also comprise at least one second gene which codes for selection agent resistance, at least one gene which codes for at least one screenable marker, and combinations thereof.

In one preferred embodiment of the present invention, meristematic tissues may be treated with at least one compound which induces the virulence of A. tumefaciens. Suitable compounds include, but are not limited to acetosyringone or other plant extracts for inducing A. tumefaciens virulence. Other additives may be applied to enhance successful infection, including, but not limited to opines such as octapine, nopaline, and leucinopine. Treatment with such virulence inducing compounds may be conducted by co-cultivating the tissue in media comprising such compounds. The tissues are incubated at a suitable incubation temperature as outlined above for a suitable time period as outlined above. In an alternative embodiment, the co-cultivation is not conducted in the presence of a virulence-inducing compound. In one embodiment, the transformed tissue is planted and allowed to grow. In a preferred alternative embodiment, the transformed tissue is incubated in conditions which allow for selection using techniques well known to those skilled in the art. For example, the tissue may be incubated in a selective regeneration medium. Selection using at least one antibiotic resistance gene may be used. Insertion of at least one antibiotic resistance gene sequence such as, but not limited to kanamycin, chloramphenicol, neomycin, carbenicillin, hygromycin and combinations thereof may be employed. Also, at least one gene coding for herbicide resistance may be inserted. These include herbicides such as, but not limited to, phosphinothricin, glyphosate, and at least one of the sulfonylureas and combinations thereof. The selective regeneration medium will be comprised of at least one suitable selective ingredient such as appropriate antibiotics for selection of antibiotic-resistant transformants, or at least one herbicide, for herbicide-resistant transformants. The choice of selective agent(s) will depend on the resistance gene transferred into the plant.

Emerging Musa regenerates may be transferred to regeneration medium comprising antibiotics and/or herbicides to allow selection of transgenic plantlets. Regeneration media are those media known to those skilled in the art which provide conditions favorable for regenerating plantlets. Suitable regeneration media include, but are not limited to, MS media, as described in Novak, F. J., et al., Bio/Technology 7, 154 (February 1989), incorporated herein by reference. Emerging regenerates are allowed to incubate for a sufficient time in the regeneration medium. A sufficient time is that which allows the formation of plantlets.

Growing Musa regenerates may then be transferred to a rooting medium. Rooting media are those media known to those skilled in the art which provide conditions favorable for inducing the formation of roots. Suitable rooting media include, but are not limited to, SH medium as described by Novak, F. J., et al., supra, incorporated herein by reference. Growing regenerates are allowed to incubate for a sufficient time in the rooting medium. A sufficient time is that which allows the formation of roots.

In a preferred embodiment, Musa regenerates are assayed for the presence of the added gene(s), or its product(s), by standard biochemical methods.

These are at least three principal advantages of the method developed for transformation of Musa spp. First is its applicability to all commercial cultivars of banana and plantain. In addition, the method allows the introduction of genes into banana or plantain without going through a cell stage that can induce somaclonal variation. In addition, the total process of gene introduction to regeneration of plants is short (less than about two months).

The method of the present invention may be used to transform the Musa plant with one or more genes. As used herein "Gene(s)" include, but are not limited to naturally occurring nucleotide sequences or synthetic nucleotide sequences. "Nucleotide sequence" as used herein refers to a chain of natural or modified nucleic acids as commonly recognized by those having skill in the art.

In order to improve the ability to identify transformants, one may desire to employ selectable or screenable marker gene as, or in addition to, the expressible gene of interest. Such genes may encode either a selectable or screenable marker, depending on whether the marker confers a trait which one can select for by chemical means, i.e., through the use of a selective agent such as an herbicide, antibiotic or the like, or whether it is simply a trait that one can identify through observation or testing (e.g., the R-locus trait). Many examples of suitable marker genes are known to the art and can be employed in the practice of the present invention.

Possible selectable markers for use in connection with the present invention include, but are not limited to, a NPT-II gene which codes for kanamycin resistance and can be selected for using kanamycin, G418, etc.; a bar gene which codes for bialaphos resistance, a mutant EPSP synthase gene which encodes glyphosate resistance; etc. Exemplary screenable markers include beta-glucuronidase (GUS), chloramphenicol acetyl transferase (CAT) or an R-locus gene, which encodes a product that regulates the production of anthocyanin pigments (red color) in host cells. Included within the terms "selectable" or "screenable marker" genes are also genes which encode a secretable marker whose secretion can be detected as a means of identifying or selecting for transformed host cells. Examples include markers which are able to secrete antigen(s) that can be identified by antibody interaction, or an enzme(s) which can be detected catalytically.

The choice of the particular gene(s) to be delivered to the plant will often depend on the purpose of the transformation. Gene(s) coding for polypeptide(s) non-native to Musa, gene (s) coding for polypeptide(s) native to Musa, gene(s) which alter gene expression and combinations thereof may be applied to Musa. Gene(s) which alter gene expression include, but are not limited, gene(s) which code for at least one ribozyme, gene(s) which code for antisense nucleotides, and gene(s) which operate as a transwitch, such as described in U.S. Pat. No. 5,231,020.

The method may be used to transform plants with genes which code for polypeptide(s) non-native to the Musa plant. As used herein, "polypeptide" refers to polypeptide or protein. This includes the production of important proteins or other products for commercial use, such as lipase, melanin, pigments, antibodies, hormones, pharmaceuticals such as, but not limited to, interleukins, EPO, G-CSF, GM-CSF, hPG-CSF, M-CSF, Factor VIII, Factor IX, tPA, hGH, receptors, insulin, vaccines, antibiotics and the like. Useful vaccines include, but are not limited to hepatitis B surface antigen and Norwalk virus capsid protein. The genes may also code for fusion proteins. The coding sequences for proteins that can be used are known in the art or can be obtained by standard sequencing techniques. Alternatively, the method may be used to produce an enzyme that is able to convert a natural product to a unique product. This includes, for example, the production of secondary metabolites useful as pharmaceuticals. Alternatively, the method may be used to alter cellular metabolism leading to altered flavor of fruit(s) or altered plant pigmentation or other phenotypic trait(s) of the plant. Such traits include, but are not limited to, visible traits, environmental or stress related traits, disease related traits, and ripening traits. These include, for example, genes responsible for the synthesis or metabolism of peptides, proteins, fatty acids, lipids, waxes, oils, starches, sugars, carbohydrates, flavors, odors, fragrances, toxins, carotenoid pigments, hormones, cell wall polymers, gene regulatory molecules, flavonoids, storage proteins, phenolic acids, coumarins, alkaloids, quinones, lignins, glucosinolates, tannins, aliphatic amines, celluloses, polysaccharides, glycoproteins and glycolipids.

For instance, an alteration in the production of fatty acids or lipids can be engineered (and fatty acid composition of, e.g., an oil-producing plant thus altered) by blocking synthesis of a specific chain elongation or desaturation enzyme. Also, the synthesis of starch can be altered and sugars altered (and sugar content of, e.g., an edible plant thus altered). Similarly, production of volatile molecules which confer fragrance can be manipulated.

In an alternative embodiment, the method is used for the transformation of plants to add some commercially desirable, agronomically important traits to the plant. Such traits include, but are not limited to, herbicide resistance, increased yields, insect and disease resistance, physical appearance, food content and makeup, etc. For example, one may desire to incorporate one or more genes encoding herbicide resistance. The bar and glyphosate tolerant EPSP synthase genes are good examples. A potential insect resistance gene which can be introduced includes the *Bacillus thuringiensis* crystal toxin gene, which may provide resistance to pests such as lepidopteran or coleopteran.

Genes encoding proteins characterized as having potential insecticidal activity, such as the cowpea trypsin inhibitor (CpTI); may find use as a rootworm deterrent; genes encoding avermectin may prove particularly useful as a corn rootworm deterrent.

In some instances, the transformed Musa plant will be chimeric. "Chimeric" refers to a plant having tissue of diverse genetic constitution, or an individual composed of a mixture of genetically different cells. Chimeric plants may, for example, be the result of the insertion of at least one gene which codes for at least one polypeptide non-native to the Musa plant, at least one gene which codes for at least one polypeptide native to the Mousa plant, at least one gene which codes for altered gene expression of at least one native Musa gene, and combinations thereof, into a region of the plant genome which leads to diminished, incomplete, or altered gene expression in only a portion of the cells which are contained in the resultant transgenic plant. In addition, chimeric plants may result from the transformation of a single cell of a meristem in which said meristem (composed of a transformed and nontransformed cells) regenerates into a "chimeric" transformed plant. Chimeric plants can be identified by techniques known to those skilled in the art. These include, but are not limited to enzymatic analyses of the foreign gene product, Southern and Northern hybridization analyses, and histochemical analyses of tissues of different cellular lineages within the same transformed plant. In some cases, chimeric plants can be identified by visual observation of plant features. For example, selected sections of the plant may have stunted or diminished growth.

In some of these cases, known to those of skill in the art, it will be desirable to develop a Musa plant that does not have these chimeric features. Generation of a nonchimeric transformed plant from a chimeric transformed plant may be effected by growing a transformed Musa plant for a sufficient time to identify the presence of chimeric features, and producing nonchimeric tissue by dividing said transformed chimeric Musa plant into segments which have at least one meristem which can regenerate into an intact plant and which have cells that are uniformly transformed to produce nonchimeric tissue, and growing said nonchimeric tissue into a nonchimeric plant. "Sufficient time" as used herein is a time known to those of skill in the art, and includes, but is not limited to about two days to about 45 days, preferably about 10 days to about 30 days, and most preferably about 14 days to about 21 days. "Dividing" as used herein refers to physical cutting, such as by a knife, scalpel or microtome.

The following examples illustrate the teachings of the present invention and are not intended as limiting the scope of the invention.

EXAMPLE 1

This example describes the transformation of banana using *Agrobacterium tumefaciens*. Neomycin phosphotransferase-II (NPT-II) and Beta-glucuronidase (GUS) were expressed in bananas.

Tissue-culture plantlets of the commercial Cavendish clone 'Grand Nain' (AAA) were micropropagated as shoot-tip cultures. Suspension cultures derived from pro-embryogenic calli were generated and maintained as described by Novak, F. J., et al., *Bio/Technology*, 7, 154–159 (1989), incorporated by reference herein.

Meristematic tips (2–5 mm in size) were excised from in-vitro shoot tip cultures to obtain the meristematic dome with 2–4 leaf primordia and a limited amount of underlying corm tissue; these were then bisected longitudinally. Alternatively, excised corm tissues (which contained numerous adventitious buds) deprived of the apical meristem were cut into slices of 2–3 mm thickness.

The plasmid pBI141 contained the GUS gene under the control of the rice actin 1 (Act1) promoter and the NPT-II gene under the control of the NOS promoter. This binary vector was constructed by inserting the XhoI/XbaI fragment of pAct1 F into XbaI/HindIII digested pBI100. The plasmid pB3G contained both the bar and GUS genes under control of the cauliflower mosaic virus 35S promoter.

Longitudinal bisections of apical ineristem or adventious bud tissues of growing banana shoot cultures were bombarded with naked micro-particles in a custom designed apparatus at a distance of 10 cm. Bombardment with naked micro-particles prior to incubation of the tissues with Agrobacterium further enhanced the percentage of plantlets which grew on selective media. These tissues underwent a three day recovery period. Following recovery, the meristematic or adventitious bud portions were co-cultivated for 30 minutes with a dilute (1:10) overnight culture of the Agrobacterium strain LBA4404, harboring pBI141, in the presence of 100 μM acetosyrinpone (AS). After inoculation, the plant tissues were transferred to non-selective S27 regeneration medium as described by Novak, F. J., et al., *Bio/Technology*, 7, 154–159 (1989), incorporated by reference herein, containing 100 μM AS, and were incubated in the dark at 27° C. for four days. Meristematic or advantious bud tissues were then transferred to selective regeneration medium containing 100 mg per liter kanamycin sulfate and 500 mg per liter carbenicillin. Regeneration shoots were transferred to rooting medium as described by Novak, supra, containing 100 mg/l kanamycin sulfate and 500 mg/l carbenicillin. Plantlets forming roots on selective medium were assayed for NPT-II activity.

Preliminary experiments were conducted using bisected apical meristems or corm tissues which were incubated with Agrobacterium in the presence or absence of acetosyringone (AS). It was found that AS increased the number of regenerating plantlets that were resistant to selective agents, indicating that AS enhanced the Agrobacterium-mediated genetic transformation of banana cells.

Putative banana transformants were assayed for the presence of NPT-II activity according to a modified protocol as described by Peng, J. Wen, et al., *Plant Mol. Biol. Rep.*, 11(1), 38–47, (1993), incorporated by reference herein. In the modification, leaf tissue from plantlets rooting on selective medium were isolated and immediately frozen in liquid $N_2$. Protein extracts were prepared by homogenizing samples in disposable Kontes tissue grinders in the presence of extraction buffer (50 mM Na phosphate buffer, pH 7.0, 10 mM β-mercaptoethanol, 10 mM EDTA, 0.2% Triton-X100). Samples were centrifuged for four minutes at 4° C., and 50 μl of each extract was added to separate microcentrifuge tubes. Remaining procedures of the assay were performed as stated by Peng, et al.

Plants in which NPT-II activities were detected were further analyzed for the presence of GUS enzymatic activity according to standard methods as described by Jefferson, R. A., *Plant Mol. Biol. Rep.*, 5, 387–405 (1987), incorporated by reference herein.

Genomic DNA was isolated from leaves of plantlets which displayed NPT-II activity according to a CTAB protocol as described by Feinberg, A. P. and Vogelstein, B., *Anal. Biochem.*, 132, 6–13 (1983), incorporated by reference herein. DNA samples (10 μg) were digested with the appropriate restriction enzymes and were electrophoresed through a 0.7% agarose gel, and transferred to a Zeta Probe™ (BioRad, Richmond, Calif.) nylon membrane according to the suppliers' recommendations. Random primed radiolabled probes were generated from the 1.0 kb EcoRV/SstI GUS fragment. Membranes were hybridized and washed as recommended by the supplier. Results were visualized by autoradiography using standard techniques.

Transformation experiments typically involved 50 micropropagated banana plantlets from which 100 bisected apical meristems and 20 to 40 corm pieces were obtained. Following co-cultivation with Agrobacterium, all plantlet regeneration steps included kanamycin sulfate as the selective agent (100 mg/l). Seventy percent of the apical meristem pieces formed shoots on micropropagation medium; 50% of these gave vigorous root growth on the selective root regeneration medium. Forty percent of the corm slices formed shoots on the selective micropropagation medium and of these, 40% formed roots on the selective root regeneration medium. Plantlets that formed roots on this selective medium were assayed for enzymatic activity of NPT-II (FIG. 1). Approximately 66% of the plants selected demonstrated easily detectable levels of enzymatic activity.

Figure 2:
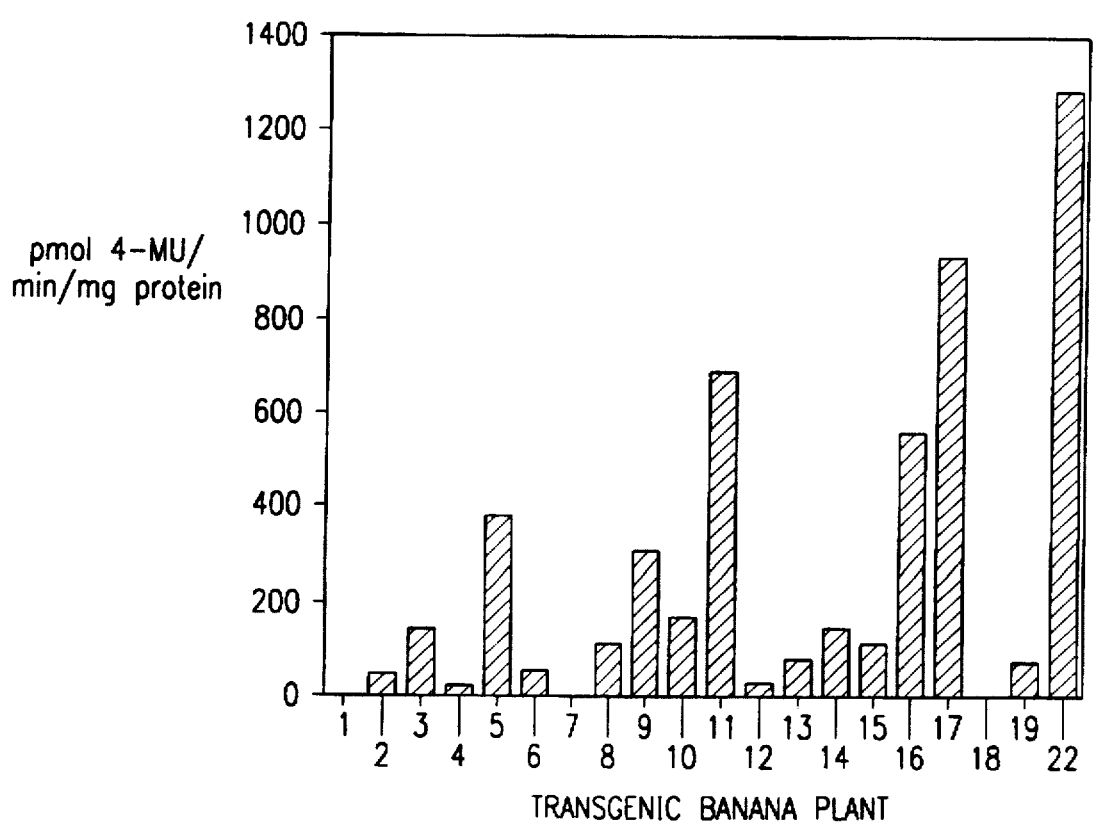
FIG. 2 depicts β-glucuronidase (GUS) activity in extracts of leaf tissue from individual plants derived from Agrobacterium-mediated transformation of banana meristematic tissues. Individual plants are identified by number. GUS activity is measured fluorimetrically as the rate of molar conversion of the substrate [4-methyl-umbelliferyl-β-D-glucuronide (MUG)] to the product [4-methyl umbelliferone (4-MU)] by the enzyme β-glucuronidase. This activity is expressed as moles of product produced per minute per mg of total protein contained in the assay mixture.

Putative transgenic banana plantlets, selected on the basis of root growth on kanamycin-containing medium and high levels of NPT-II activity were further evaluated for GUS enzymatic activity (FIG. 2). Leaf tissue from non-transformed controls demonstrated low-level background GUS activities (average value of 20 picomoles of 4-methyl umbeflliferone/min/mg protein). Individual transformants expressed a range of GUS activities, from levels near those of non-transformed controls to over 1000 picomoles of 4-methyl umbelliferone/min/mg protein.

Figure 3:
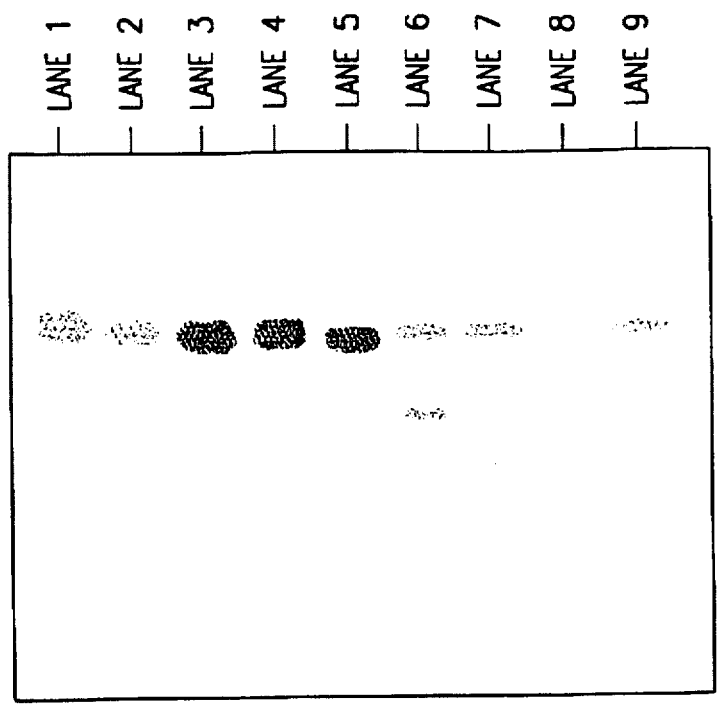
FIG. 3 depicts an autoradiograph of a Southern blot of genomic DNA from negative control (non-transformed), positive control (transgenic tobacco plants harboring NTP-II), and banana plants transformed by Agrobacterium which were regenerated on 100 mg/l kanamycin. Ten micrograms of each genomic DNA were EcoRI digested and were loaded onto separate lanes. These DNAs were hybridized against a 1.0 kb PstI fragment of NPT-II. DNA from plants (transgenic banana and transgenic tobacco) which exhibit NPT-II activity (lanes 1 thru 7 and lane 9), demonstrated hybridization to the NPT-II fragment. The non-transformed (negative control) banana plant (lane 8) demonstrated no detectable hybridization.

Genomic DNAs from control and putative transgenic plants were isolated and analyzed for the presence of the NPT-II gene (FIG. 3). Ten micrograms of genomic DNA from each sample was digested with the indicated restriction enzyme and were hybridized to the 1.0 kb NPT-II fragment. Each of the regenerates tested, which had previously been found to demonstrate NPT-II activity, contained sequences that hybridized to the NPT-II fragment.

Figure 4:
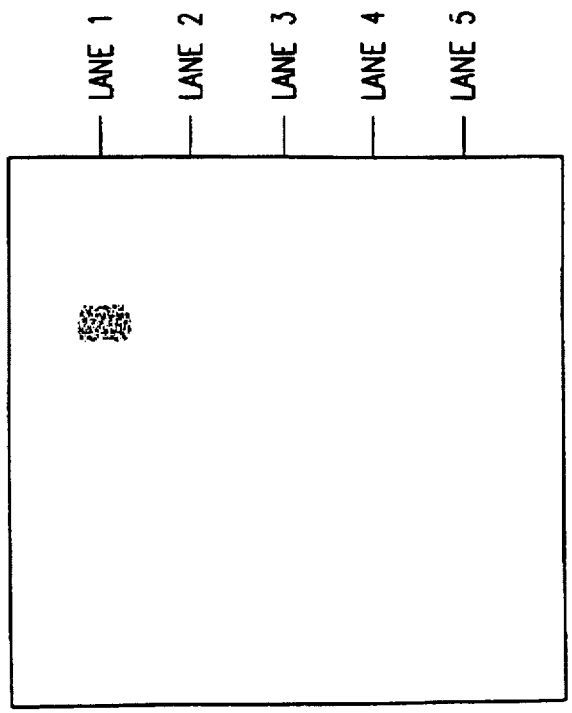
FIG. 4 depicts an autoradiograph of a Southern blot of genomic DNA from positive control (Agrobacterium genomic DNA), negative control (non-transformed banana plants), and banana plants transformed by Agrobacterium which were regenerated on 100 mg/l kanamycin. One microgram of the Agrobacterium DNA and 10 ug of the plant DNAs were EcoRI digested and were loaded onto separate lanes. These DNAs were hybridized against a 1.0 kb Bam HI/BagIII fragment containing vir B. DNA from Agrobacterium demonstrated hybridization to the vir B fragment (lane 1). Neither the non-transformed (negative control) banana plant (lane 2), nor the transgenic banana plants (lanes 3–5) demonstrated detectable hybridization.

To determine if the hybridizations of the NPT-II fragment in tested samples were due to the presence of contaminating residual Agrobacterium, genomic DNAs from the above samples were hybridized with the bacterial virulence gene vir B. No hybridization of vir B was detected in the regenerated plant samples, while a positive control lane containing Agrobacterium genomic DNA gave an easily detectable signal (FIG. 4).

EXAMPLE 2

In this Example, meristematic tissue was treated as described in Example 1, with the exception that the tissue was transformed with an *A. tumefaciens* harboring a plasmid having the gene encoding the hepatitis B surface antigen (HBsAG) in lieu of GUS.

The construction of the Ti vector encoding HBsAG (pHB101) was described previously [Mason, et al., *Proc. Natl. Acad. Sci. USA* 89, 11745–11749 (1992)] and the sequence of the HBsAG gene used in the construct has been published [Pasek, et al., *Nature* 282, 575–579 (1979)]. Agrobacterium strain LBA4404 cells were transformed by the direct method [An, et al., *Methods Enzymol.* 153, 292–305 (1987)], incorporated by reference herein, with the plasmids prepared from *E. coli* clones, and the structure of the plasmids was verified by restriction digestion. Meristematic tissues were transformed as described in Example 1 by Agrobacterium with the plasmid pHB101 (encoding the HBsAG). Plantlets were selectively regenerated on 100 mg/l kanamycin. These putative transformants could be rooted on media containing 100 mg/l of the selective agent, whereas non-transformed controls died under these conditions.

Protein was extracted from leaf tissues by homogenization with a Ten-Broek ground glass homogenizer (clearance, 0.15 mm) in 5 volumes of buffer containing 20 mM sodium phosphate (pH 7.0), 0.15M NaCl, 20mM sodium ascorbate, 0.1% Triton X-100, and 0.5 mM phenylmethylsulfonyl fluoride at 4° C. The homogenate was centrifuged at 1000×g for 5 min, and the supernatant was centrifuged at 27,000×g for 15 min. The 27,000×g supernatant was centrifuged at 100,000×g for 1 hr, and the pellet was resuspended in extraction buffer. Protein in the different fractions was measured by the Coomassie dye-binding assay (Bio-Rad). HBsAG was assayed with the Auszyme monoclonal kit (Abbott, North Chicago, Ill.), using the positive control (HBsAG derived from human serum) as a standard. The positive control was diluted to give HBsAG levels of 0.09–1.8 ng per assay, and the absorbance at 492 nm after color development gave a linear relationship in this range.

Plantlets regenerated on selection media were assayed for the presence of HBsAG. Antigenic positive material was detected in Musa plants transformed with pHB101.

EXAMPLE 3

This is a prophetic example. Meristematic tissue is transformed with an *A. tumefaciens* harboring a plasmid having the gene encoding phosphinothricin acetyltransferase and GUS. The bar gene encodes phosphinothricin acetyltransferase (PAT);

which when introduced into transgenic plants gives resistance to the herbicide Basta. The sequence of the bar gene used in the construction of the Ti-plasmid encoding PAT was recently published [White, et al., *Nuc. Acids. Res.* 64, 675–678 (1990)]. A plasmid (pDE110) containing the bar gene under the control of the cauliflower mosaic virus (CaMV) promoter and the nopaline synthase (NOS) terminator is used in the generation of a Ti plasmid (pIBT-115), containing sequences that encode PAT. The EcoRI/HindIII fragment containing the CaMV promoter, PAT encoding sequences and NOS terminator is released from pDE110 following an EcoRI/HindIII digestion. This fragment is treated with the DNA polymerase Klenow fragment in the presence of excess dNTPs to produce a blunt-ended fragment. PBI21 (CLONETECH Laboratories, Palo Alto, Calif.), containing the GUS gene under the control of the CaMV promoter, is linearized by digestion with the restriction enzyme Pst I. Following digestion, the resulting 3'-OH protrusion is removed from the plasmid by treatment with T4 DNA polymerase in the presence of excess dNTPs at 12° C. Collectively, these treatments result in a linear plasmid (pBI121) having blunt ends. In addition, this treatment results in the release of a majority of the NPT-II gene and its NOS terminator which resides on the PstI/PstI fragment of pBI121. The blunt-ended EcoRI/HindIII CaMV-PAT-NOS fragment is ligated into the NPT-II-less pBI121 to yield pIBT-115. Agrobacterium strain LBA4404 cells are transformed by the direct method [An, et al., *Methods Enzymol.* 153, 292–305 (1987)] with the plasmids prepared from *E. coli* clones, and the structure of the plasmids is verified by restriction digestion. Meristematic tissues are transformed by Agrobacterium with the plasmid pIBT115 (encoding both the bar and GUS genes) as described in Example 1, with the exception that phosphinothricin is substituted for kanamycin as the selective agent. Plantlets are selectively regenerated on 0.5 mg/l phosphinothricin. These putative transformants can be rooted on media containing 0.5 mg/l of the herbicide, whereas non-transformed controls die under these conditions. Some of the plants are subsequently grown in soil and tested for herbicide resistance by direct application of the chemical into the leaf whorl when the plants have grown to about a 10 cm height. Severe injury to non-transformed controls is evident in leaf browning while putative transformants show no visible symptoms. It is also observed that herbicide application to control plants cause inhibition of the apical meristem growth with a concomitant proliferation of daughter plants ("suckers"); these affects are not observed in the putative transformants. Since pIBT115 encodes the GUS gene, we also conducted histochemical staining experiments on these plants to score for the presence of GUS. Intense staining was observed in all herbicide resistant plants as compared to no staining in non-transformed controls under the same conditions of histochemical assay.

EXAMPLE 4

The transformation of meristems derived as per Example 1 may result in chimeric plants. That is, only one cell in a cluster of cells might receive the NPT II DNA, but the resulting enzymatic activity might result in kanamycin degradation that would protect the surrounding cells, thus allowing regeneration of a plant that would contain both transformed and non-transformed cells. To create conditions to eliminate any possible non-transformed cells and cell-derivatives, two additional levels of selection pressure may be used—a rooting regime in the presence of the selection agent, followed by one or more additional rounds of shoot regeneration that force new plant formation from only a small cluster of cells.

For these experiments, 3×5 mm shoot tips and 2–3 mm thick corm slices were excised from the rooted putative transformants plants recovered on 100 mg/l kanamycin following Agrobacterium co-cultivation. These were transferred to shooting medium which also contained the same level of kanamycin. For comparison, non-transformed control meristems or corm slices were transferred to a range of kanamycin concentrations, up to and including 100 mg/l. Inhibition effects in the control plants included stunting of growth and yellowing of leaves; at 100 mg/l, root growth was totally inhibited. A portion of the putative transformants showed vigorous root growth on this level of inhibitor. In a typical experiment, about 40% of the tissues which formed roots on kanamycin formed vigorous roots. These data indicate that the remaining 60% were chimeric, and did not contain meristematic tissues that would give rise to antibiotic-resistant roots. In some cases, following prolonged exposure of putative transformants to kanamycin selection on rooting medium (more than 4 weeks), the death of most of the meristematic shoot tissue was observed in individual samples, with a subsequent onset of new shoot and root development arising from only a small portion of the previously green tissues. We interpret this phenomenon to be the death on non-transformed tissues, coupled with growth of a new plantlet arising from meristematic tissue derived from an original progenitor cell line which had resulted from an Agrobacterium-mediated transformation event.

It was important to determine if the plantlets which had regenerated and rooted on 100 mg/l kanamycin showed evidence of enzymatic activity corresponding to antibiotic degradation. We analyzed multiple individual transformants obtained after Agrobacterium-mediated transformation with pBI141, which includes the NPT II gene.

Plantlets that formed roots on the selective medium were assayed for enzymatic activity of NPT (Peng et al., supra). Approximately 66% of the putative transformants which formed roots on selective media demonstrated easily detectable levels of enzymatic activity.

Individual plants were selected on the basis of these NPT assays for further propagation; the plants which had demonstrated high levels of enzymatic activities were subjected to further meristem culture. This involved dissection of each putative transformants into a small apical meristem and corm slices; these tissues were then transferred to shooting medium containing 100 mg/l kanamycin. Vigorously growing green shoots were subsequently selected, dissected into small (3×5 mm) apical meristems and corm slices, and allowed to develop into new shoots which were subsequently forced to root on 100 mg/l kanamycin. From the original 50 plants which were used to start a typical experiment, approximately five vigorously growing putative transformants were obtained after this second round of rooting selection. These were then individually analyzed by further enzymatic and Southern analysis and in all cases, the apical meristem tissue was always preserved and micropropagated to derive multiple clonally propagated derivatives.

Many other variations and modifications may be made in the techniques herein before described, by those having skill in this technology, without departing from the concept of the present invention. Accordingly, it should be clearly understood that the foregoing description is illustrative only, and not intended as a limitation on the scope of the invention.

We claim:

1. A method for transforming a Musa plant, said method comprising:
   a. wounding meristematic tissue from a Musa plant to generate a wounded Musa plant tissue and to facilitate access of *Agrobacterium tumefaciens* to Musa plant cells competent for transformation and regeneration; and
   b. applying to said wounded Musa plant tissue at least one transformation competent *Agrobacterium tumefaciens* to transform said Musa plant, wherein said at least one transformation competent *Agrobacterium tumefaciens* harbors at least one Ti plasmid and at least one virulence gene, wherein said at least one Ti plasmid comprises at least one genetically engineered T-DNA to effect transformation of said Musa plant.

2. The method according to claim 1, wherein the at least one genetically engineered T-DNA comprises at least one first gene selected from the group consisting of genes which code for at least one polypeptide non-native to the Musa plant, genes which code for at least one polypeptide native to the Musa plant, genes which alter expression of at least one native Musa gene, and combinations thereof.

3. The method according to claim 2, wherein the at least one genetically engineered T-DNA further comprises at least one second gene selected from the group consisting of genes which code for selection agent resistance, genes which code for at least one screenable marker, and combinations thereof.

4. The method according to claim 2, wherein the at least one genetically engineered T-DNA further comprises at least one gene which codes for selection agent resistance, and wherein the method further comprises regenerating the transformed Musa plant tissue in the presence of at least one selection agent responsive to the at least one gene which codes for selection agent resistance so as to select for resistant tissue transformed with the at least one genetically engineered T-DNA.

5. The method according to claim 1, wherein the Musa plant is selected from the group consisting of banana and plantain.

6. The method according to claim 1, wherein the meristematic tissue is selected from the group consisting of apical meristem, adventitious meristem, and combinations thereof.

7. The method according to claim 1, wherein the wounding is by dissection.

8. The method according to claim 1, further comprising bombarding the meristematic tissue with microparticles prior to applying the at least one transformation competent *Agrobacterium tumefaciens*, but after wounding the meristematic tissue.

9. The method according to claim 1, further comprising co-cultivating the wounded Musa plant tissue with *Agrobacterium tumefaciens* and at least one compound for inducing the at least one virulence gene of *Agrobacterium tumefaciens*.

10. The method according to claim 9, wherein the at least one compound for inducing the at least one virulence gene of *Agrobacterium tumefaciens* is acetosyringone.

11. The method according to claim 2, wherein the at least one first gene which codes for at least one polypeptide non-native to the Musa plant codes for resistance to at least one herbicide.

12. The method according to claim 11, wherein the at least one herbicide is selected from the group consisting of phosphinothicin, glyphosate, sulfonylureas, and combinations thereof.

13. The method according to claim 2, wherein the at least one first gene which codes for at least one polypeptide non-native to the Musa plant codes for at least one pharmaceutical.

14. The method according to claim 13, wherein the at least one pharmaceutical is selected from the group consisting of hepatitis B surface antigen, Norwalk virus capsid protein, interleukins, growth hormone, erythropoietin, G-CSF, GM-CSF, hPG-CSF, M-CSF, Factor VIII, Factor IX, tPA, insulin, and combinations thereof.

15. The method according to claim 3, wherein the at least one second gene which codes for at least one screenable marker is selected from the group consisting of GUS, CAT, and combinations thereof.

16. The method according to claim 3, wherein the at least one second gene which codes for selection agent resistance codes for antibiotic resistance.

17. The method according to claim 16, wherein the at least one second gene which codes for antibiotic resistance codes for resistance to at least one antibiotic selected from the group consisting of kanamycin, hygromycin, and combinations thereof.

18. The method according to claim 3, wherein the at least one second gene which codes for selection agent resistance codes for herbicide resistance.

19. The method according to claim 18, wherein the at least one second gene which codes for herbicide resistance codes for resistance to at least one herbicide selected from the group consisting of phosphinothricin, glyphosate, sulfonylureas, and combinations thereof.

20. The method according to claim 1, wherein the at least one genetically engineered T-DNA codes for at least one industrial enzyme.

21. The method according to claim 1, wherein the at least one genetically engineered T-DNA codes for at least one fusion protein.

22. The method according to claim 1, wherein the at least one genetically engineered T-DNA codes for at least one protein that interacts with at least one compound in the Musa plant to produce a secondary metabolite of said at least one compound.

23. The method according to claim 1, wherein the at least one genetically engineered T-DNA codes for at least one protein that changes at least one phenotypic trait of the fruit of the Musa plant.

24. The method according to claim 23, wherein at least one phenotypic trait is selected from the group consisting of texture, flavor, pigmentation, and combinations thereof.

25. The method according to claim 23, wherein the at least one phenotypic trait affects the ripening of the fruit of the Musa plant.

26. A Musa plant produced by the method of claim 1, which comprises cells which comprise in their genome at least one gene selected from the group consisting of at least one gene which codes for at least one polypeptide nonnative to the Musa plant, at least one gene which codes for at least one polypeptide native to the Musa plant, at least one gene which codes for altered gene expression of at least one native Musa gene, and combinations thereof.

27. A method according to claim 1, further comprising:

a) growing said transformed Musa plant for a sufficient time to identify the presence of chimeric features;

b) producing nonchimeric tissue by dividing said transformed Musa plant into segments which have at least one meristem which can regenerate into an intact plant and which have cells that are uniformly transformed to produce nonchimeric tissue; and c) growing said nonchimeric tissue into a nonchimeric plant.

28. A transformed plant made by the method of claim 1.

29. Vegetatively-derived progeny of the transformed plant of claim 26.

30. Plant parts obtained from the transformed plant of claim 26.

* * * * *